US010912812B2

(12) United States Patent
Huber et al.

(10) Patent No.: US 10,912,812 B2
(45) Date of Patent: Feb. 9, 2021

(54) METHODS FOR PREPARING BOTANICAL EXTRACTS

(71) Applicant: Signum Biosciences, Inc., Monmouth Junction, NJ (US)

(72) Inventors: Kristen Huber, Monmouth Junction, NJ (US); Michael Voronkov, Monmouth Junction, NJ (US); Jose Fernandez, Monmouth Junction, NJ (US); Karl Rouzard, Monmouth Junction, NJ (US); Eduardo Perez, Monmouth Junction, NJ (US); Maxwell Stock, Monmouth Junction, NJ (US); Jeffry Stock, Monmouth Junction, NJ (US)

(73) Assignee: Signum Biosciences, Inc., Monmouth Junction, NJ (US)

( * ) Notice: Subject to any disclaimer, the term of this patent is extended or adjusted under 35 U.S.C. 154(b) by 0 days.

(21) Appl. No.: 16/514,337

(22) Filed: Jul. 17, 2019

(65) Prior Publication Data
US 2019/0336561 A1 Nov. 7, 2019

Related U.S. Application Data

(62) Division of application No. 15/327,875, filed as application No. PCT/US2015/041621 on Jul. 22, 2015, now abandoned.

(60) Provisional application No. 62/027,607, filed on Jul. 22, 2014.

(51) Int. Cl.
A61K 8/97 (2017.01)
A61K 36/9066 (2006.01)
A61K 36/77 (2006.01)
A61K 36/87 (2006.01)
A61K 36/33 (2006.01)
A61K 36/73 (2006.01)
A61K 45/06 (2006.01)
A61K 9/00 (2006.01)
A61K 36/14 (2006.01)
A61K 36/185 (2006.01)
A61K 36/23 (2006.01)
A61K 36/235 (2006.01)
A61K 36/28 (2006.01)
A61K 36/31 (2006.01)
A61K 36/45 (2006.01)
A61K 36/52 (2006.01)
A61K 36/54 (2006.01)
A61K 36/575 (2006.01)
A61K 36/71 (2006.01)
A61K 36/736 (2006.01)
A61K 36/79 (2006.01)
A61Q 19/08 (2006.01)

(52) U.S. Cl.
CPC ............ *A61K 36/9066* (2013.01); *A61K 8/97* (2013.01); *A61K 9/0014* (2013.01); *A61K 9/0053* (2013.01); *A61K 36/14* (2013.01); *A61K 36/185* (2013.01); *A61K 36/23* (2013.01); *A61K 36/235* (2013.01); *A61K 36/28* (2013.01); *A61K 36/31* (2013.01); *A61K 36/33* (2013.01); *A61K 36/45* (2013.01); *A61K 36/52* (2013.01); *A61K 36/54* (2013.01); *A61K 36/575* (2013.01); *A61K 36/71* (2013.01); *A61K 36/73* (2013.01); *A61K 36/736* (2013.01); *A61K 36/77* (2013.01); *A61K 36/79* (2013.01); *A61K 36/87* (2013.01); *A61K 45/06* (2013.01); *A61Q 19/08* (2013.01); *A61K 2236/00* (2013.01); *A61K 2236/31* (2013.01); *A61K 2236/33* (2013.01); *A61K 2236/331* (2013.01); *A61K 2236/39* (2013.01); *A61K 2236/51* (2013.01); *A61K 2236/53* (2013.01); *A61K 2800/5922* (2013.01); *A61K 2800/782* (2013.01); *A61K 2800/805* (2013.01); *A61K 2800/92* (2013.01)

(58) Field of Classification Search
None
See application file for complete search history.

(56) References Cited

U.S. PATENT DOCUMENTS 6,159,986 A 12/2000 Altman
6,312,738 B1 * 11/2001 O'Shea ................ C07D 519/00
424/761
7,491,414 B2 2/2009 Wang
(Continued)

FOREIGN PATENT DOCUMENTS

IN 2010CH02241 A * 6/2012

OTHER PUBLICATIONS

Janssens et al., Protein phosphatase 2A: a highly regulated family of serine/threonine phosphatases implicated in cell growth and signalling. Biochem J. Feb. 1, 2001,353(Pt 3):417-39.
(Continued)

*Primary Examiner* — Ralph J Gitomer
(74) *Attorney, Agent, or Firm* — Kim IP Law Group LLC

(57) ABSTRACT

Method of preparing a botanical extract that includes contacting a raw botanical with a solvent having a dielectric constant ranging from about 2.3 to about 25 and allowing the mixture to reside for a sufficient time to obtain a crude extract; filtering out remaining raw botanical and evaporating the solvent from the crude extract under reduced pressure to obtain a dried crude extract; washing the dried crude extract with a polar solvent having a dielectric constant of no less than 30, heating the resulting mixture, and allowing to cool to ambient; collecting a filtrate from the above cooled mixture; washing the collected filtrate with a non-polar solvent having a dielectric constant of no more than 2.0; and filtering and drying the mixture to obtain the botanical extract.

5 Claims, 2 Drawing Sheets

(56) References Cited

U.S. PATENT DOCUMENTS

| 7,794,965 | B2 | 9/2010 | Stock et al. | |
|---|---|---|---|---|
| 7,923,041 | B2* | 4/2011 | Stock | A23G 3/36 |
| | | | | 424/725 |
| 8,034,389 | B2 | 10/2011 | Nawar | |
| 9,084,755 | B2* | 7/2015 | Sun | C07D 493/20 |
| 2003/0186416 | A1 | 10/2003 | Pallas et al. | |
| 2005/0277694 | A1 | 12/2005 | Stock et al. | |
| 2008/0213406 | A1 | 9/2008 | Stock et al. | |
| 2008/0227842 | A1* | 9/2008 | Krautler | A61P 17/00 |
| | | | | 514/414 |
| 2009/0264496 | A1 | 10/2009 | Vafai et al. | |
| 2009/0274682 | A1 | 11/2009 | Shi et al. | |
| 2011/0117187 | A1 | 5/2011 | Stock et al. | |
| 2011/0280852 | A1 | 11/2011 | Miller | |
| 2017/0042958 | A1* | 2/2017 | Du | A61K 9/0014 |

OTHER PUBLICATIONS

Kamibayashi et al., Comparison of heterotrimeric protein phosphatase 2A containing different B subunits. J Biol Chem. Aug. 5, 1994;269(31):20139-48.

Sangodkar et al., All roads lead to PP2A: exploiting the therapeutic potential of this phosphatase. FEBS J. Mar. 2016;283(6):1004-24. Published online Nov. 14, 2015.

Selhub et al., Serum total homocysteine concentrations in the third National Health and Nutrition Examination Survey (1991-1994): population reference ranges and contribution of vitamin status to high serum concentrations. Ann Intern Med. Sep. 7, 1999,131(5):331-9.

Seshadri et al., Plasma homocysteine as a risk factor for dementia and Alzheimer's disease. N Engl J Med. Feb. 14, 2002;346(7):476-83.

Sontag et al., Altered expression levels of the protein phosphatase 2A ABalphaC enzyme are associated with Alzheimer disease pathology. J Neuropathol Exp Neurol. Apr. 2004;63(4):287-301.

Tolstykh et al., Carboxyl methylation regulates phosphoprotein phosphatase 2A by controlling the association of regulatory B subunits. EMBO J. Nov. 1, 2000;19(21):5682-91.

Vafai et al., Protein phosphatase 2A methylation: a link between elevated plasma homocysteine and Alzheimer's Disease. FEBS Lett. May 8, 2002;518(1-3):1-4.

Wei et al., Carboxymethylation of the PP2A catalytic subunit in *Saccharomyces cerevisiae* is required for efficient interaction with the B-type subunits Cdc55p and Rts1p. J Biol Chem. Jan. 12, 2001;276(2):1570-7.

Wu et al., Carboxyl methylation of the phosphoprotein phosphatase 2A catalytic subunit promotes its functional association with regulatory subunits in vivo. EMBO J. Nov. 1, 2000;19(21):5672-81.

Yu et al., Methylation of the protein phosphatase 2A catalytic subunit is essential for association of Balpha regulatory subunit but not SG2NA, striatin, or polyomavirus middle tumor antigen. Mol Biol Cell. Jan. 2001;12(1):185-99.

International Search Report for International Application No. PCT/US2015/041621 dated Nov. 23, 2015.

Written Opinion for International Application No. PCT/US2015/041621 dated Nov. 23, 2015.

Hernandez-Perez et al., Biochemical and Nutritional Characterization of Three Prickly Pear Species with Different Ripening Behavior, Plant Foods for Human Nutrition, 2005, p. 195-200, vol. 60, Springer Science+Business Media Inc.

Edwards, H. et al. Analytical Raman Spectroscopic Study of Cacao Seeds and Their Chemical Extracts. Analytica Chi mica Acta 538(1-2)175-180, May 4, 2005. (Year: 2005).

Elkhori, S. et al. The Microwave Assisted Process: Extraction and Determination of Fat from Cocoa Powder and Cocoa Nibs. J of Food Engineering 79(3)1110-1114, 2007. (Year: 2007).

Bachovchin D. et al. Discovery and Optimization of Sulfonyl Acrylonitriles as Selective Covalent Inhibitors of Protein Phosphatase Methylesterase-1. J of Medicinal Chemistry 54:5229-5236, 2011. (Year: 2011).

* cited by examiner

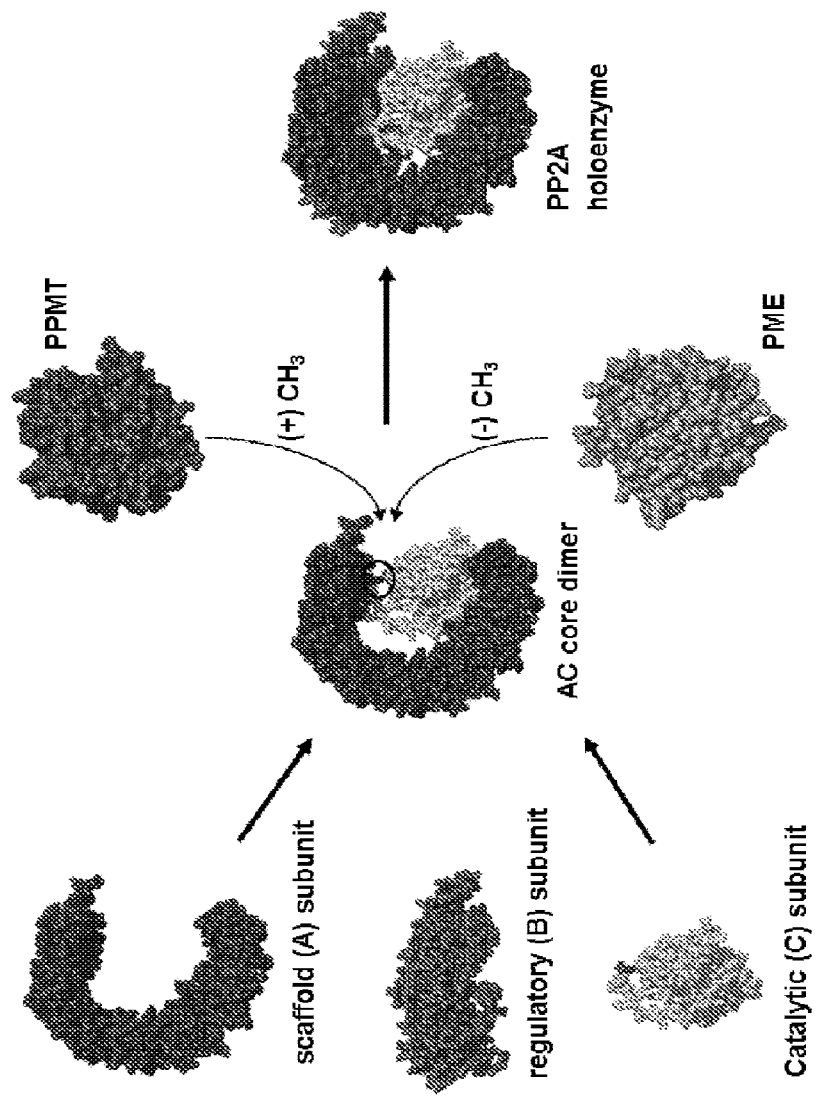
Figure 1: PP2A assembly and methylation.

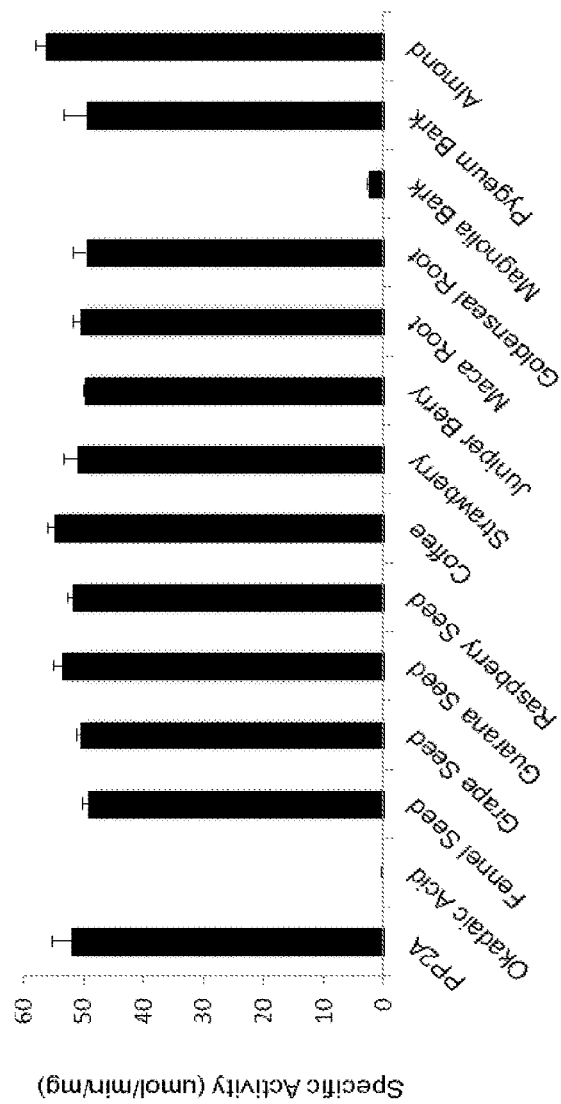
Figure 2: Natural extracts affect on PP2A-AC phosphatase activity.

METHODS FOR PREPARING BOTANICAL EXTRACTS

RELATED APPLICATIONS

This application is a divisional application of U.S. application Ser. No. 15/327,875, filed Jan. 20, 2017, which is a 35 U.S.C. § 371 national stage filing of International Application No. PCT/US2015/041621, filed Jul. 22, 2015, which claims the benefit of U.S. Provisional Application No. 62/027,607, filed Jul. 22, 2014. Each of these prior-filed applications are herein incorporated by reference in their entirety.

FIELD OF THE INVENTION

The present invention relates to compositions containing natural and botanical extracts for use in inhibiting demethylation of PP2A by PME-1 methylesterase; formation of free radicals and reactive oxygen species; and/or inflammation.

BACKGROUND

Protein phosphatase 2A (PP2A), a major serine/threonine phosphatase, has been implicated in a broad range of cellular functions anywhere from development to disease. Consisting of a scaffolding (A), regulatory (B) and catalytic (C) subunit, as shown in FIG. 1, this trimeric holoenzyme is highly regulated through structural assembly, post-translational modifications and small molecule interactions. Methylation of PP2A's carboxy-terminal tail has not only been implicated in modulating its activity and specificity but it has also been shown to be of particular importance in neurodegenerative diseases such as Alzheimer's and Parkinson's disease. For this reason, modulators of PP2A's methylation state are of particular importance.

Protein phosphatase 2A (PP2A) associates with a variety of regulatory subunits. (Janssens, V., Gloris, J., Biochem. J. 353 (Pt. 3): 417-39 (2001)). The predominant form in neuronal tissue is a trimer composed of a dimeric core composed of a 65 kilodalton (kDa) A subunit and the 36 kDa PP2A catalytic C subunit associated with one of several different regulatory B subunits. Whereas the A and C subunits are present more or less uniformly, the B subunit is variable and confers substrate specificity and subcellular localization to each PP2A holoenzyme trimer. The number and types of B suhunits present is subject to developmental regulation and is cell type specific.

The variable B subunits of PP2A are classified into four families: (1) the B family with four isoforms ($\alpha$, $\beta$, $\gamma$, $\delta$); (2) the B' family with five isoforms ($\alpha$, $\beta$, $\gamma$, $\delta$, $\epsilon$); (3) the B" family; and (4) the B'" family. The PP2A AB$\alpha$C heterotrimer appears to be the major phosphatase in brain responsible for dephosphorylation of tau. (Kamibayashi, C. et al., J. Biol. Chem. 269 (31): 20139-148 (1994); Sontag, E., et al., J. Neuropathol. Exp. Neurol. 63 (4): 287-301 (2004)).

The alpha-carboxyl of the C terminal leucine residue of the catalytic subunit of PP2A is subject to methyl esterification and methyl-ester hydrolysis, and the methylation state of PP2A regulates heterotrimer formation. (Tokstykh, T. et al., EMBO J. 19 (21): 5682-91 (2000); Wu, J. et al., EMBO J. 19 (21): 5672-81 (2000); Wei, H. et al., J. Biol. Chem. 276 (2): 1570-77 (2001); Yu, X X, ct al., Mol. Biol. Cell 12 (1): 185-99 (2001)). Two enzymes are involved in controlling the methylation state of PP2A: (1) an S-adenosylmethionine-dependent PP2A-specific protein methyltransferase ("PPMT"), which adds the methyl group and (2) a PP2A-specific protein methylesterase ("PPME"), which removes the methyl group. PP2A methylation promotes PP2A AB$\alpha$C trimer assembly. Any deficiency in methylation is expected to preclude PP2A AB$\alpha$C heterotrimer formation, thereby leading to a deficiency in tau dephosphorylation, tau hyperphosphorylation and the formation of neurofibrillary tangles. (Vafai, S. B., Stock, J. B., FEBS Lett. 518 (1-3): 1-4 (2002)).

Homocysteine, a sulfur-containing amino acid that can be either remethylated to methionine or undergo a trans-sulfuration reaction to cystathionine, plays a key role in methylation metabolism (see FIG. 1). The conversion of homocysteine to methionine occurs in all tissues. Methionine is activated by ATP in the presence of methionine adenosyl transferase to form the methyl donor, S-adenosylmethionine ("SAM"). SAM-dependent methylation reactions in the presence of SAM-dependent methyltransferases result in the formation of S-adenosylhomocysteine ("SAH"), which is cleaved by SAH hydrolase to form adenosine and homocysteine. This reaction is reversible with the equilibrium favoring the condensation of homocysteine and adenosine. Under normal conditions, homocysteine is rapidly methylated, which favors the further cleavage of SAH. Homocysteine accumulation leads to global decreases in cellular methylation by the condensation of homocysteine with adenosine to form SAH, which acts as a product inhibitor in cellular methylation reactions. In the United States, 5-10% of the general population has elevated plasma homocysteine, and this imbalance increases to 30-40% in of the elderly. (Selub J., et al., Ann. Intern. Med. 131 (5): 331-39 (1999)). See Vafai, S. B., Stock, J. B., FEBS Lett. 2: 518 (2002).

Over the last several years, data has emerged in clinical literature suggesting a direct association between elevated plasma homocysteine and the occurrence of AD. Seshadri et al., (N Enel J Med 346 (7): 476-83 (2002)), demonstrated that elevated homocysteine is a risk factor for AD. After adjusting for other AD risk factors, the study concluded that plasma homocysteine levels greater than 14 $\mu$M coincided with about a 2-fold increased risk for developing AD with an additional 40% increased risk with each 5 $\mu$M incremental rise. Other diseases, conditions or disorders associated with elevated plasma homocysteine include, but are not limited to, atherosclerosis; neurodegenerative disorders, such as Parkinson's disease; cerebrovascular disorders (i.e., disorders pertaining to blood vessels in the brain), such as stroke; neuropsychiatric disorders, such as bipolar disorder and schizophrenia; diabetes (type 11), and arthritis.

An analysis of the clinical and basic science literature indicates that a methylation defect resulting from elevated homocysteine could lead to lowered levels of PP2A methylation that would result in lowered PP2A AB$\alpha$C, which is believed to lead to tau hyperphosphorylation, neurofibrillary tangle formation, and dementia (Vafai and Stock, FEBS Lett 518(1-3): 1-4 (2002)).

Cellular pathways for removing plasma homocysteine require folate, Vitamin $B_6$ and $B_{12}$, and thus high homocysteine levels are expected in mice fed diets deficient in these components. This was demonstrated using, male C57BL/J6 mice. One set of 4 week old mice were placed on a diet that contained folate, vitamin $B_6$, and vitamin $B_{12}$ and another set were fed diets that lacked these vitamins. The mice were allowed free access to both food and water. After nine weeks on their respective diets, each mouse was sacrificed by cervical dislocation. Blood samples were collected for measurement of plasma homocysteine and the brain was removed and quickly frozen in liquid nitrogen for further analysis of tau phosphorylation. As expected the vitamin-deficient diets caused substantial increases in plasma Hcy and brain SAH. These increases were accompanied by elevated levels of Tau phosphorylation. CP13 and PHF1 are monoclonal antibodies that are specific for phosphorylated tau epitopes. TG5 is a monoclonal antibody that recognizes tau independent of its state of phosphorylation; it thereby provides a control showing that total levels of tau expression are unaffected by diet. Mice raised on diets deficient in folate, $B_{12}$, and $B_6$ had dramatically elevated levels of total plasma homocysteine, brain S-adenosyl homocysteine and elevated levels of tau phosphorylation. S-Adenosyl methionine levels were not significantly affected.

The demographics of aging in the United States population, combined with a lack of effective treatments, have heightened the need for AD therapies. Moreover, the development of preventives would be an even greater contribution to public health. A protective agent that could be taken over many years to reduce the risk of AD or to substantively delay its onset would be an invaluable breakthrough.

BRIEF SUMMARY OF THE INVENTION

One aspect of the present invention provides compositions containing natural and botanical extracts for use in inhibiting one, two, or three of (a)-(c): (a) demethylation of PP2A by PME-1 methylesterase; (b) formation of free radicals and reactive oxygen species; and/or (c) inflammation. These compositions include an extract of one or more botanicals selected from the group consisting of: juniper berry fruit, schisandra fruit, strawberry fruit, avocado seeds, black raspberry seeds, blueberry seeds, celery seeds, cranberry seeds, fennel seeds, grape seeds, guarana seeds, red raspberry seeds, maca root, goldenseal root, turmeric root, magnolia bark, pygeum bark, red raspberry leaf, almond, cocoa powder, *Echinacea angustifolia*, prickly pear cactus and walnut.

In one particularly preferred embodiment, the compositions contain a combination of extracts that inhibit all three of (a) demethylation of PP2A by PME-1 methylesterase; (b) formation of free radicals and reactive oxygen species; and (c) inflammation. The combination of extracts can be combined in a single composition.

Another aspect of the present invention provides a method of preparing a botanical extract that includes introducing a raw botanical to a solvent having a dielectric constant ranging from about 2.3 to about 25 and allowing the mixture to reside for a sufficient time to obtain a crude extract. The method further includes filtering out remaining raw botanical and evaporating the solvent from the crude extract under reduced pressure to obtain a dried crude extract, and washing the dried crude extract with a polar solvent having a dielectric constant of no less than 30 (e.g., water), heating the resulting mixture, and allowing to cool. The method can further include collecting a filtrate from the cooled mixture mentioned above and washing the collected filtrate with a non-polar solvent having a dielectric constant of no more than 2.0 (e.g., cyclohexane, hexane, heptane and isooctane). The method can further include filtering and drying the mixture mentioned above to obtain the botanical extract.

Another aspect of the present invention provides a method for inhibiting demethylation of PP2A by PME-1 methylesterase comprising administering to a subject in need thereof an effective amount of a botanical extract. Subjects that are in need of inhibition of demethylation of PP2A by PME-1 methylesterase, and hence can be administered the presently disclosed extracts or compositions, include, but are not limited to, subjects that exhibit, or are at risk for exhibiting, Tau hyper-phosphorylation, α-synculein hyper-phosphorylation, and/or abnormally elevated homocysteine levels.

In another aspect of the present invention, the subject exhibits, or is at risk for exhibiting, a skin disorder, medical condition or disease. In one embodiment, the subject desires to maintain healthy skin and prevent skin aging.

Another aspect of the present invention provides a method for inhibiting inflammation in a subject comprising administering to a subject an effective amount of a botanical extract.

Another aspect of the present invention provides a method for inhibiting the formation of free radicals and reactive oxygen species in a subject comprising administering to a subject an effective amount of a botanical extract obtained from at least one source selected from the group consisting of grape seed, guarana seed, red raspberry seed, prickly pear cactus and turmeric root.

Any one of the above-described extracts, and compositions containing these extracts, can be, in certain embodiments, topically administered, such as, for example, as a cream, lotion, cleanser, ointment or other pharmaceutically acceptable topical dosage form. Alternatively, any one of the above-described extracts, and compositions containing these extracts, can be, in certain embodiments, orally administered, such as, for example, as a pill, tablet, capsule, syrup or a drink or other pharmaceutically acceptable oral dosage form. In either topical or oral form, the extract can be administered together with other botanicals and vitamins.

The invention is further directed to the general and specific embodiments defined, respectively, by the Numbered Embodiments appended hereto, which are incorporated by reference herein.

BRIEF DESCRIPTION OF THE DRAWINGS

FIG. 1 presents a flow chart of PP2A assembly and methylation.

FIG. 2 presents a bar graph of PP2A-AC phosphatase activity.

DETAILED DESCRIPTION OF THE INVENTION

The invention can be more fully appreciated by reference to the following description, including the examples. Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described herein. In addition, the materials, methods, and examples are illustrative only and not intended to be limiting.

For the sake of brevity, all publications, including patent applications, patents, and other citations mentioned herein, are incorporated by reference in their entirety. Citation of any such publication, however, shall not be construed as an admission that it is prior art to the present invention.

Terms and Definitions

As used herein, the term "about" or "approximately" means within an acceptable range for a particular value as determined by one skilled in the art, and may depend in part on how the value is measured or determined, e.g., the limitations of the measurement system or technique. For example, "about" can mean a range of up to 20%, up to 10%, up to 5%, or up to 1% or less on either side of a given value. Alternatively, with respect to biological systems or processes, the term "about" can mean within an order of magnitude, within 5 fold, or within 2 fold on either side of a value. Numerical quantities given herein are approximate unless stated otherwise, meaning that the term "about" or "approximately" can be inferred when not expressly stated.

To provide a more concise description, some of the quantitative expressions given herein are not qualified with the term "about." It is understood that, whether the term "about" is used explicitly or not, every quantity given herein is meant to refer to both the actual given value and the approximation of such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity for which that could be obtained under the particular stoichiometric conditions. Concentrations that are given as percentages refer to mass ratios, unless indicated differently.

As used herein, the terms "a," "an," and "the" are to be understood as meaning both singular and plural, unless explicitly stated otherwise. Thus, "a," "an," and "the" (and grammatical variations thereof where appropriate) refer to one or inure.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof, unless limitation to the singular is explicitly stated.

The terms "comprising" and "including" are used herein in their open, non-limiting sense. Other terms and phrases used in this document, and variations thereof, unless otherwise expressly stated, should be construed as open ended, as opposed to limiting. Thus, the term "example" is used to provide exemplary instances of the item in discussion, not an exhaustive or limiting list thereof. Similarly, adjectives such as "conventional," "traditional," "normal," "criterion," "known," and terms of similar meaning should not be construed as limiting the item described to a given time period or to an item available as of a given time, but they should be read to encompass conventional, traditional, normal, or criterion technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. As will become apparent to one of ordinary skill in the art after reading this document, the illustrated embodiments and their various alternatives may be implemented without confinement to the illustrated examples.

The term "composition" is intended to encompass a product including the herein described extracts and the inert ingredient(s) (pharmaceutically acceptable excipients) that make up the carrier, as well as any product which results, directly or indirectly, from combination, complexation, or aggregation of any two or more of the ingredients, or from dissociation of one or more of the ingredients, or from other types of reactions or interactions of one or more of the ingredients. In certain embodiments, a "composition," as used herein, is pharmaceutically acceptable and suitable for oral administration. In alternative embodiments, a "composition," as used herein, is pharmaceutically acceptable and suitable for topical administration.

The term "carrier" refers to an adjuvant, vehicle, or excipients, with which the compound is administered. In certain embodiments of this invention, the carrier is a solid carrier. Suitable pharmaceutical carriers include those described in Remington: The Science and Practice of Pharmacy, $21^{st}$ Ed., Lippincott Williams & Wilkins (2005).

The term "dosage form," as used herein, is the form in which the dose is to be administered to the subject or patient. The active extract is generally administered as part of a formulation that includes nonmedical agents. The dosage form has unique physical and pharmaceutical characteristics. Dosage forms, for example, can be solid, liquid, gel or gaseous. "Dosage forms" may include for example, a capsule, tablet, caplet, gel caplet (gelcap), syrup, a liquid composition, a powder, a concentrated powder, a concentrated powder admixed with a liquid or topical gel or lotion, a chewable form, a swallowable form, a dissolvable foim, an effervescent, a granulated form, a topical form and an oral liquid solution. In a specific embodiment, the dosage form is a solid dosage form, and more specifically, comprises a tablet or capsule. In another specific embodiment, the dosage form is a topical dosage form, and more specifically, comprises a gel, lotion or other form suitable for application to human skin.

The term "pharmaceutically acceptable," as used in connection with compositions of the invention, refers to molecular entities and other ingredients of such compositions that are physiologically tolerable and do not typically produce untoward reactions when administered to an animal (e.g., human) according to their intended mode of administration (e.g., oral or topical).

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluents to facilitate administration of an agent and that is compatible therewith. Examples of excipients include calcium carbonate, calcium phosphate, various sugars and types of starch, cellulose derivatives, gelatin, vegetable oils, and polyethylene glycols. Suitable pharmaceutical carriers include those described in Remington: The Science and Practice of Pharmacy, 2E' Ed., Lippincott Williams & Wilkins (2005).

As used herein, the term "inert" refer to any inactive ingredient of a described composition. The definition of "inactive ingredient" as used herein follows that of the U.S. Food and Drug Administration, as defined in 21 C.F.R. 201.3(b)(8), which is any component of a drug product other than the active ingredient.

As used herein, "suitable for oral administration" or "suitable for topical administration" refers to a sterile, pharmaceutical product produced under good manufacturing practices (UMP). The term "suitable for oral administration"

or "suitable for topical administration" can, when specified, also mean approved by a regulatory agency of the Federal or a state government or listed in the U.S. Pharmacopeia or other generally recognized pharmacopeia for use in animals (e.g. mammals), and more particularly in humans.

As used herein, the term "raw botanical" as used herein refers to a fresh or processed (e.g. cleaned, frozen, dried, sliced, dissolved, or liquefied) part of a single species of plant or natural material, or a fresh or processed alga or macroscopic fungus. Raw botanicals can be commercially obtained from, for example, Prickly Pear Products, LLC, Mesa, Ariz., Starwest Botanicals, Sacramento, Calif., www-.HerbStoreUSA.com, Frontier Natural Products CO-OP, and www.znaturalfoods.com.

As used herein, the term "disorder" is used interchangeably with "disease" or "condition". For example, a neurological disorder also means a neurological disease or a neurological condition.

The terms "treat," "treating," and "treatment" cover therapeutic methods directed to a disease-state in a subject and include: (i) preventing the disease-state from occurring, in particular, when the subject is predisposed to the disease-state but has not yet been diagnosed as having it; (ii) inhibiting the disease-state, e.g., arresting its development (progression) or delaying its onset; and (iii) relieving the disease-state, e.g., causing regression of the disease state until a desired endpoint is reached. These terms also include ameliorating a symptom of a disease (e.g., reducing the pain, discomfort, or deficit), wherein such amelioration may be directly affecting the disease (e.g., affecting the disease's cause, transmission, or expression) or not directly affecting the disease.

As used in the present disclosure, the term "effective amount" is interchangeable with "therapeutically effective amount" and means an amount or dose of a compound or composition effective in treating the particular disease, condition, or disorder disclosed herein, and thus "treating" includes producing a desired preventative, inhibitory, relieving, or ameliorative effect. In methods of treatment according to the invention, "an effective amount" of at least one compound is administered to a subject (e.g., a mammal). The "effective amount" will vary, depending on the compound, the disease (and its severity), the treatment desired, age and weight of the subject, etc.

As used herein, the phrase "in combination" refers to agents that are simultaneously administered to a subject. It will be appreciated that two or more agents are considered to be administered "in combination" whenever a subject is simultaneously exposed to both (or more) of the agents. Each of the two or more agents may be administered according to a different schedule; it is not required that individual doses of different agents be administered at the same time, or in the same composition. Rather, so long as both (or more) agents remain in the subject's body, they are considered to be administered "in combination".

As used herein, the term "modulate" refers to change in a parameter (e.g., a change in a binding interaction or an activity, etc.). Modulation can refer to an increase or a decrease in the parameter (e.g., an increase or decrease in binding, an increase or decrease in activity, etc.).

As used herein, the term "modulator" refers to an agent that alters level and/or activity of its target (e.g., in the GPCR signal transduction pathway). In some embodiments, a modulator alters interaction between a protein in the GPCR signal transduction pathway and one or more other entities. In some embodiments, a modulator alters interaction between a modulator alters interaction between a protein in the GPCR signal transduction pathway and a substrate. Determination of whether an agent is a modulator can be performed directly or indirectly. Determination of whether an agent modulates an interaction can be performed directly, e.g., using an assay that detects the interaction between a protein in the GPCR signal transduction pathway and a substrate. Determination of whether an agent modulates an interaction can be performed with a technique that indirectly detects modulation, e.g., a technique that detects a biological activity that is downstream of, and dependent on, the protein-substrate interaction.

As used herein, the term "skin irritant" refers to a extract that, when applied to skin or a skin equivalents, elicits a cellular response characterized by the expression of an "irritant responsive gene." Examples of known skin irritants include, but are not limited to, sodium dodecyl sulfate ("SDS"), calcipotriol, and trans-retinoic acid. The term "skin irritant" is also intended to encompass unknown or suspected irritants, including hut not limited to, those containing in some pharmaceuticals, cosmetics, and consumer products. In embodiments of the present invention, the presently disclosed compositions are free of, or substantially free of, skin irritants.

The terms "individual," "subject," and "patient" are used interchangeably herein and can be a vertebrate, in particular, a mammal, more particularly, a primate (including non-human primates and humans) and include a laboratory animal in the context of a clinical trial or screening or activity experiment. Thus, as can be readily understood by one of ordinary skill in the art, the compositions and methods of the present invention are particularly suited to administration to any vertebrate, particularly a mammal, and more particularly, a human.

As used herein, the term "cognitive function" refers to the ability to perform mental tasks, such as thinking, learning, judging, remembering, computing, controlling motor functions, and the like. The expression "resilience of cognitive function" refers to the ability of functional elements of cognitive function to resist deterioration over time. As used herein, the term "cognitive function enhancing amount" refers to that amount of the composition of the present invention that will noticeably impact the ability to perform mental tasks, as measured by tests for memory, computation, attention, or other mental or cognitive attribute, or as suggested by an individual's perception of his or her abilities in these realms.

As used herein, the term "G-protein mediated condition" refers any disease or other deleterious condition for which the appearance, incidence, and/or severity of one or more symptoms correlates with changes in a G-protein signaling cascade. In some embodiments, one or more symptoms of the disease or condition is caused by a defect or alteration in G-protein signaling.

As used herein, the term "comestible" refers to a material that is suitable for human consumption, including a material that can be ingested by oral and by a non-oral means, e.g., an inhalant or a snuff. For purposes of the present invention, the term includes supplemented or enhanced foods.

The terms "dietary supplement" and "nutritional supplement" are used interchangeably herein to mean (1) a product intended to supplement the diet that bears or contains one or more of the following dietary ingredients: [A] a vitamin, [B] a mineral, [C] an herb or other botanical, [D] an amino acid, [E] a dietary substance for use by man to supplement the diet by increasing the total dietary intake; or (F) a concentrate, metabolite, constituent, extract, or combination of any ingredient described in clause (A), (B), (C), (D), or (E); and (2)

a product that (A)(i) is intended for ingestion; (B) is not represented for use as a conventional food or as a sole item of a meal or the diet; and (C) is labeled as a dietary supplement.

The term "health" or "healthy" as used herein refers to a general condition of the body or mind with reference to soundness and vigor, as well as freedom from disease or ailment.

The term "partitioning" as used herein refers to a process that takes advantage of the differential solubility of a substance in two solvents.

The terms "soluble" and "solubility" refer to the property of being susceptible to being dissolved in a specified fluid (solvent). The term "insoluble," as used herein refers to the property of a material that has minimal or limited solubility in a specified solvent.

The term "solvent" as used herein refers to a substance, usually liquid, capable of dissolving or dispersing one or more other substances. Chemists have classified solvents into two broad categories according to their polarity: polar and nonpolar. A common measure of the polarity of a solvent is the dielectric constant. The term "polar solvent" as used herein refers to a compound that is composed of polar molecules. A "polar molecule" is one in which there is some separation of charge in the chemical bonds, so that one part of the molecule has a slight positive charge and the other a slight negative charge. Polar solvents may be further classified as protic or aprotic. The term "protic" refers to a hydrogen atom attached to an electronegative atom, while the term "aprotic" refers to a molecule that does not contain an O—H bond. A "polar protic solvent" can be represented by the general formula ROH; the polarity of the polar protic solvent stems from the bond dipole of the O—H bond. Examples of polar protic solvents include, but are not limited to, water, alcohols, and acetic acid. A "dipolar aprotic solvent" is one that contains a bond that has a large bond dipole. Typically, this bond is a multiple bond between carbon and either oxygen or nitrogen. Most dipolar aprotic solvents contain a C—O double bond. Examples of dipolar aprotic solvents include, but are not limited to, acetone and ethyl acetate. As the number of —CH2- groups in ROH increases, and the relative amount of hydrocarbon character increases, the polarity decreases. The term "nonpolar solvent" refers to compounds that have low dielectric constants and are not miscible with water. Examples of nonpolar solvents include, but are not limited to, benzene, carbon tetrachloride, and hexanes.

The term "well-being" as used herein refers to a subject's physical and mental soundness.

A composition of the present invention, alone or in combination with other active ingredients, may be administered to a subject in a single dose or multiple doses over a period of time, generally by oral or topical administration. As used herein, the terms "therapeutically effective amount," "memory-enhancing amount", and "cognition enhancing amount" refer to the amount of the composition of the invention that results in a therapeutic or beneficial effect, including a subject's perception of health or general well-being, following its administration to a subject.

It is believed that an increase in the level of PP2A methylation, or PP2A modulation in general, will bring about the protection or enhancement of cognitive functioning, or preventing a cognitive disorder from manifesting or deepening. Thus the therapeutic effect of the compositions of the present invention can exert a protective or enhancing effect on cognitive function; minimize, prevent or ameliorate cognitive symptoms of a disease or disorder, or may have any other beneficial effect.

The concentration of the substance is selected so as to exert its therapeutic effect, but low enough to avoid significant side effects within the scope and sound judgment of the skilled artisan. The effective amount of the composition may vary with the age and physical condition of the biological subject being treated, the severity of the condition, the duration of the treatment, the nature of concurrent therapy, the specific compound, composition or other active ingredient employed, the particular carrier utilized, and like factors. Those of skill in the art can readily evaluate such factors and, based on this information, determine the particular effective concentration of a composition of the present invention to be used for an intended purpose.

A skilled artisan can determine a therapeutically effective amount of the inventive compositions by determining the unit dose. As used herein, a "unit dose" refers to the amount of inventive composition required to produce a response of 50% of maximal effect (i.e. ED50). The unit dose can be assessed by extrapolating from dose-response curves derived from in vitro or animal model test systems. The amount of compounds in the compositions of the present invention which will be effective in the treatment of a particular disorder or condition will depend on the nature of the disorder or condition, and can be determined by standard clinical techniques. (See, for example, Goodman and Gilman's The Pharmacological Basis of Therapeutics, Joel G. Harman, Lee E. Limbird, Eds.; McGraw Hill, New York, 2001; The Physician's Desk Reference, Medical Economics Company, Inc., Oradell, N.J., 1995; and Drug Facts and Comparisons, Facts and Comparisons, Inc., St. Louis, Mo., 1993). The precise dose to be employed in the formulation will also depend on the route of administration, and the seriousness of the disease or disorder, and should be decided according to the judgment of the practitioner and each patient's circumstances. Various administration patterns will be apparent to those skilled in the art.

The dosage ranges for the administration of the compositions of the present invention are those large enough to produce the desired therapeutic effect. Preferably, the cognitive function enhancing amount of the compositions of the present invention is administered one or more times per day on a regular basis. A typical dose administered to a human is between about 1 mg and about 10 g of the composition, preferably between 1 mg and 1 g of the composition.

Those skilled in the art will recognize that initial indications of the appropriate therapeutic dosage of the compositions of the invention can be determined in in vitro and in vivo animal model systems, and in human clinical trials. One of skill in the art would know to use animal studies and human experience to identify a dosage that can safely be administered without generating toxicity or other side effects. For acute treatment where it is desirable to substantially increase methylated PP2A, it is preferred that the therapeutic dosage be close to the maximum tolerated dose. For chronic preventive use, lower dosages may be desirable because of concerns about long term effects. However, the instant extracts are commonly believed to be safe and have a history of human use. Alternatively, the composition of the present invention may be administered at least once per day in combination with a prescribed drug. For example, the composition of the present invention may be administered together with existing anti-cholinesterase drugs now prescribed for Alzheimer's, with various anti-inflammatory agents, or with statins.

Reference will now be made to the embodiments of the present invention, examples of which are illustrated by and described in conjunction with the accompanying examples. While certain embodiments are described herein, it is understood that the described embodiments are not intended to limit the scope of the invention. On the contrary, the present disclosure is intended to cover alternatives, modifications, and equivalents that can be included within the invention as defined by the appended numbered embodiments.

One aspect of the present invention provides compositions containing natural and botanical extracts for use in inhibiting one, two, or three of (a)-(c): (a) demethylation of PP2A by PME-1 methylesterase; (b) formation of free radicals and reactive oxygen species; and/or (c) inflammation. These compositions include an extract of one or more botanicals selected from the group consisting of: juniper berry fruit, schisandra fruit, strawberry fruit, avocado seeds, black raspberry seeds, blueberry seeds, celery seeds, cranberry seeds, fennel seeds, grape seeds, guarana seeds, red raspberry seeds, maca root, goldenseal root, turmeric root, magnolia hark, pygeum hark, red raspberry leaf, almond, cocoa powder, *Echinacea angustifolia*, prickly pear cactus and walnut.

In embodiments in which the compositions inhibit demethylation of PP2A by PME-1 methylesterase, or that modulate PP2A, the compositions can include an extract of one or more of juniper berry fruit, schisandra fruit, strawberry fruit, avocado seeds, black raspberry seeds, blueberry seeds, celery seeds, cranberry seeds, fennel seeds, grape seeds, guarana seeds, red raspberry seeds, maca root, goldenseal root, turmeric root, magnolia bark, pygeum bark, red raspberry leaf, almond, cocoa powder, *Echinacea angustifolia*, prickly pear cactus and walnut. In alternative embodiments in which the compositions inhibit demethylation of PP2A by PME-1 methylesterase, the compositions can include an extract of one or more of grape seed, guarana seed, red raspberry seed, prickly pear cactus, and turmeric root.

One embodiment of the present invention provides compositions comprising a methylation modifying compound isolated from a raw botanical material (i) that inhibits at least one enzyme that demethylates PP2A, wherein the composition inhibits at least 50%, more preferably by at least 90%, of the demethylating activity of the demethylating enzyme as measured by levels of PP2A methyl esterification; or (ii) that stimulates the methylating activity of at least one enzyme that methylates PP2A. In one embodiment, the botanical extract contains at least 5 units per microliter of the activity inhibiting demethylation of the protein phosphatase 2A (PP2A) enzyme and thereby stimulates methylation of the protein phosphatase 2A (PP2A) enzyme. In an alternative embodiment, the botanical extract, or extracts when used in combination, has an $IC_{50}$ value of less than 25 μg/mL, or less than 10 μg/mL, or less than 5 μg/mL, as determined according to the procedure of Example 2 herein. In one embodiment, the presently disclosed compositions modulate the PP2A enzyme.

In certain embodiments in which the compositions inhibit the formation of free radicals and reactive oxygen species, the compositions can include an extract of one or more of grape seed, guarana seed, red raspberry seed, prickly pear cactus, and turmeric root. In one embodiment, the botanical extract, or extracts when used in combination, has an $IC_{50}$ value of less than 25 μg/mL, or less than 10 μg/mL, or less than 5 μg/mL, as determined according to the procedure of Example 3 herein.

In certain embodiments in which the compositions inhibit inflammation (including, e.g., micro-inflammation) the compositions can include an extract of one or more of grape seed, guarana seed, red raspberry seed, prickly pear cactus, and turmeric root. In one embodiment, the botanical extract, or extracts when used in combination, has an $IC_{50}$ value of less than 25 μg/mL, or less than 10 μg/mL, or less than 5 μg/mL, as determined according to the procedure of Example 4 herein.

In certain embodiments, any one of the compositions set forth herein (e.g., compositions containing natural and botanical extracts for use in inhibiting one, two, or three of (a)-(c): (a) demethylation of PP2A by PME-1 methylesterase; (b) formation of free radicals and reactive oxygen species; and/or (c) inflammation) includes an extract that is obtained from a solvent having a dielectric constant ranging from about 2.3 to about 25. For example, the extract can be obtained from one or more of isopropyl alcohol, toluene, and ethyl acetate. In further embodiments, the composition includes an extract that is substantially free of polar components (e.g., caffeine, sugars, oligosaccharides, etc.) soluble in solvents with a dielectric constant no less than 30 (e.g., water). In a still further embodiment, the extract is substantially free of non-polar components (e.g., lipids, oils) soluble in solvents with a dielectric constant no more than 2.0 (e.g., cyclohexane, hexane, heptane or isooctane).

In one embodiment, the composition includes, or consists essentially of, or consists of, an extract of grape seed. In one embodiment, the composition includes, or consists essentially of, or consists of, an extract of guarana seed. In one embodiment, the composition includes, or consists essentially of, or consists of, an extract of red raspberry seed. In one embodiment, the composition includes, or consists essentially of, or consists of, an extract of prickly pear cactus. In one embodiment, the composition includes, or consists essentially of, or consists of, an extract of turmeric root.

In one embodiment, the composition includes, or consists essentially of, or consists of, an extract of grape seed and an extract of guarana seed. In one embodiment, the composition includes, or consists essentially of, or consists of, an extract of grape seed and an extract of red raspberry seed. In one embodiment, the composition includes, or consists essentially of, or consists of, an extract of grape seed and an extract of prickly pear cactus. In one embodiment, the composition includes, or consists essentially of, or consists of, an extract of grape seed and an extract of turmeric root.

In one embodiment, the composition includes, or consists essentially of, or consists of, an extract of guarana seed and an extract of red raspberry seed. In one embodiment, the composition includes, or consists essentially of, or consists of, an extract of guarana seed and an extract of prickly pear cactus. In one embodiment, the composition includes, or consists essentially of, or consists of, an extract of guarana seed and an extract of turmeric root.

In one embodiment, the composition includes, or consists essentially of, or consists of, an extract of red raspberry seed and an extract of prickly pear cactus. In one embodiment, the composition includes, or consists essentially of, or consists of, an extract of red raspberry seed and an extract of turmeric root. In one embodiment, the composition includes an extract of prickly pear cactus and an extract of turmeric root.

In one embodiment, the composition includes, or consists essentially of, or consists of, an extract of grape seed, an extract of guarana seed, and an extract of red raspberry seed. In one embodiment, the compositions includes, or consists essentially of, or consists of, an extract of grape seed, an extract of guarana seed, and an extract of prickly pear cactus. In one embodiment, the compositions includes, or consists essentially of, or consists of, an extract of grape seed, an extract of guarana seed, and an extract of turmeric root.

In one embodiment, the composition includes, or consists essentially of, or consists of, an extract of grape seed, an extract of red raspberry seed, and an extract of prickly pear cactus. In one embodiment, the compositions includes, or consists essentially of, or consists of, an extract of grape seed, an extract of red raspberry seed, and an extract of turmeric root. In one embodiment, the compositions includes, or consists essentially of, or consists of, an extract of grape seed, an extract of prickly pear cactus, and an extract of turmeric root.

In one embodiment, the composition includes, or consists essentially of, or consists of, an extract of guarana seed, an extract of red raspberry seed, and an extract of prickly pear cactus. In one embodiment, the composition includes, or consists essentially of, or consists of, an extract of guarana seed, an extract of red raspberry seed, and an extract of turmeric root. In one embodiment, the composition includes, or consists essentially of, or consists of, an extract of guarana seed, an extract of prickly pear cactus, and an extract of turmeric root. In one embodiment, the compositions include, or consists essentially of, or consists of, an extract of red raspberry seed, an extract of prickly pear cactus, and an extract of turmeric root.

In one embodiment, the composition includes, or consists essentially of, or consists of, an extract of grape seed, an extract of guarana seed, an extract of red raspberry seed, and an extract of prickly pear cactus. In one embodiment, the composition includes, or consists essentially of, or consists of, an extract of grape seed, an extract of guarana seed, an extract of red raspberry seed, and an extract of turmeric root. In one embodiment, the composition includes, or consists essentially of, or consists of, an extract of grape seed, an extract of guarana seed, an extract of prickly pear cactus, and an extract of turmeric root. In one embodiment, the composition includes, or consists essentially of, or consists of, an extract of guarana seed, an extract of red raspberry seed, an extract of prickly pear cactus and an extract of turmeric root. In one embodiment, the composition includes, or consists essentially of, or consists of, an extract of grape seed, an extract of red raspberry seed, an extract of prickly pear cactus, and an extract of turmeric root.

In one embodiment, the composition includes, or consists essentially of, or consists of, an extract of grape seed, an extract of guarana seed, an extract of red raspberry seed, an extract of prickly pear cactus, and an extract of turmeric root.

In another aspect, the composition of the present invention is administered at least once per day in combination with a dietary or nutritional supplement believed to have beneficial health effects. For example. Coenzyme Q10 (also known as CoQ10, Q10, vitamin Q10, ubiquinone and ubidecarenone), a benzoquinone compound synthesized naturally by the human body, is used by cells of the body in oxidative metabolism or cell respiration and as an endogenous antioxidant. An "antioxidant" is a substance that protects cells from free radicals, which are highly reactive chemicals often containing oxygen atoms, that are capable of damaging important cellular components, such as DNA and lipids. The plasma level of CoQ10 has been used in studies as a measure of oxidative stress, a situation in which normal antioxidant levels are reduced. Various investigations have explored the usefulness of CoQ10 as a treatment for diseases, including, but not limited to, cancer and cardiovascular disease.

Idebenone, a synthetic analog of CoQ10, has been investigated in elderly patients with dementia. Studies suggest that it may diminish nerve cell damage due to ischemia and facilitate memory and learning.

Huperzine A, a natural acetylcholinesterase inhibitor derived from the Chinese herb Huperzia serrata, has antioxidant and neuroprotective properties, and has been proposed as a disease-modifying treatment for AD.

Galantamine, an acetylcholinesterase inhibitor, is used to treat symptoms of AD.

Vincamine and vinpocetine, a semisynthetic derivative of vincamine, an alkaloid derived from the plant Vina minor L, are used in Europe, Japan and Mexico as pharmaceutical agents for the treatment of cerebrovascular and cognitive disorders.

Acetyl-L-carinitine, an acetylated derivative of carnitine, has been shown to promote fatty acid beta-oxidation in liver and to prevent motor nerve condition velocity slowing in diabetic rats.

Dehydroepiandrosterone (DHEA), a steroid, is being studied in the prevention of cancer. In the body, it is a precursor produced by the adrenal gland and converted to testosterone or the estrogens.

Phosphatidylcholine, a phospholipid that is a major component of cell membranes, has putative activity as a cognition enhancer and in cell-membrane repair.

Gingko, an herb, has putative properties as a neuroprotective agent, an antioxidant, a free-radical scavenger, a membrane stabilizer, and an inhibitor of platelet-activating factor. Sherpina, V. S., et al., American Family Physician 68(5) 923-926 (2003). Gingko extract also has been shown to inhibit beta-amyloid deposition. Id.

*Ginseng*, a Chinese herb, has been used for centuries in Asia as a cure for many maladies.

Research has shown that Vitamin E (DL-alpha-tocopherol), an essential vitamin that functions as an antioxidant, can help prevent cardiovascular disease and increase the immune response. It has been hypothesized that Vitamin E and its analogs and derivatives may prevent brain cell damage by destroying toxic free radicals. The term "tocol" generally refers to 2-methyl-2-(4,8,12-trimetyltridecyl)chroman-6-ol; the term "tocopherol" generally refers to all mono, di, and trimethyltocols, including, but not limited to, alpha-tocopherol (5,7,8-trimethyltocol), beta-tocopherol (5,8-dimethyltocol), gamma-tocopherol (7,8-dimethyltocol), delta-tocopherol (8-methyltocol), the term "tocotrienol" refers to 2-methyl-2-(4,8,12-trimethyltrideca-3,7,11-trienyl)chroman-6-ol; and the term "vitamin E" generally refers to all tocol and tocotrienol derivatives exhibiting qualitatively the biological activity of alpha-tocopherol.

It is well-known that N-acetyl-cysteine (NAC) promotes cellular glutathione production, and thus reduces, or even prevents, oxidant mediated damage. Treatment with NAC provides beneficial effects in a number of respiratory, cardiovascular, endocrine, infectious, and other disease settings.

B vitamins, such as folic acid, are known to reduce levels of homocysteine, an amino acid already linked, at high levels, to an increased risk of heart attacks, strokes and Alzheimer's disease.

Lecithin, a lipid material composed of choline and inositol, is a major component of cell membranes. As used by producers of lecithin for commercial use, the term "lecithin" refers to a complex mix of phosphatides and other substances that contain phosphatidylcholine.

Choline (trimethyl ethanolamine), a quaternary saturated amine classified as an essential nutrient by the Food and Nutrition Board of the Institute of Medicine, is a component of lecithin. Choline is needed by the body to make the neurotransmitter acetylcholine.

Fish oil, which is oil derived from the tissues of oily fish, naturally contains the omega-3 fatty acids eicosapentaenoic acid (EPA) and docosahexaenoic acid (DHA). Some experts believe that fish oil can help regulate cholesterol in the body. It also may help protect the brain from cognitive problems associated with Alzheimer's disease.

Deprenyl (selegiline, Eldepryl®), a monoamine oxidase inhibitor, is prescribed for the treatment of early-stage Parkinson's disease and senile dementia.

The compositions of the invention can be used alone or in combination with other pharmaceuticals or herbals to prolong mental health, to maintain or enhance cognitive functioning or memory, or to preserve mental or physical well-being and health. The compositions can also be used to prevent or treat effects a number of ailments, including, but not limited to, Alzheimer's disease; Parkinson's disease; heart disease; arthritis; age-related degeneration, functional impairments, and diseases; diabetes, and cancer, have on cognitive function.

The effectiveness of the compositions and methods of the present invention can be assayed by a variety of protocols. The effects of increasing cognitive function in a human subject can be determined by methods routine to those skilled in the art including, but not limited to, both paper and pencil, and computer tests. One of skill in the art can also directly measure PP2A methylation levels, tau protein phosphorylation levels, neurofibrillary tangle formation and neurodegeneration in animal models.

Another aspect of the present invention provides a method of preparing a botanical extract that includes introducing a raw botanical to a solvent having a dielectric constant ranging from about 2.3 to about 25 (e.g., isopropyl alcohol, toluene and ethyl acetate) and allowing the mixture to reside for a sufficient time (e.g., 4 hours, 8 hours, 16 hours, 24 hours, 48 hours, or as necessary) at a set temperature (e.g., from ambient to boiling point of the corresponding solvent) to obtain a crude extract. The method further includes filtering out remaining raw botanical and evaporating the solvent from the crude extract under reduced pressure to obtain a dried crude extract (e.g., via a rotary evaporator), and washing the dried crude extract with a polar solvent having a dielectric constant of no less than 30 (e.g., water), heating the resulting mixture, and allowing to cool (e.g., allow to cool to at or approaching ambient). The method can further include collecting a filtrate from the cooled mixture mentioned above and washing the collected filtrate with a non-polar solvent having a dielectric constant of no more than 2.0 (e.g., cyclohexane, hexane, heptane and isooctane). The method can further include filtering and drying the mixture mentioned above to obtain the botanical extract.

The present invention further includes compositions that include, consist essentially of, or consists of an extract obtained by any process described herein.

Another aspect of the present invention provides a method for inhibiting demethylation of PP2A by PME-1 methylesterase comprising administering to a subject in need thereof an effective amount of a botanical extract. Subjects that are in need of inhibition of demethylation of PP2A by PME-1 methylesterase, and hence can be administered the presently disclosed extracts or compositions, include, but are not limited to, subjects that exhibit, or are at risk for exhibiting, Tau hyper-phosphorylation, α-synculein hyper-phosphorylation, and/or abnormally elevated homocysteine levels. For example, the presently disclosed compositions can be administered to subjects who exhibit abnormal one carbon metabolism (e.g., subjects who have disruptions in folate, methionine and choline pathways).

According to another embodiment, the composition inhibits a demethylating activity of a demethylating enzyme that acts on a protein phosphatase 2A enzyme and thereby stimulates methylation of the protein phosphatase 2A enzyme. According to another embodiment, the composition inhibits at least about 50% of the demethylating activity of the demethylating enzyme. According to another embodiment, the demethylating enzyme is a protein phosphatase 2A specific protein methylesterase. According to another embodiment, the demethylating activity of the protein phosphatase 2A specific protein methylesterase is determined by measuring levels of protein phosphatase 2A methyl esterification.

In one embodiment, the subject in need of the presently disclosed extracts and compositions have been diagnosed with, or is at risk for developing, Alzheimer's Disease. In another embodiment, the subject in need of the presently disclosed extracts and compositions have been diagnosed with, or is at risk for developing, Parkinson's Disease.

In one embodiment, the subject is a healthy subject. For example, the healthy subject may desire to prevent cognitive and/or motor function decline, or they may wish to improve upon their present cognitive and motor function.

The invention also provides methods of enhancing memory in a human, which method includes administering a memory enhancing amount of a presently described composition (e.g., a pill, topical administration or comestible). Methods of enhancing cognitive function in a human, the method comprising the step of administering a cognitive function enhancing amount of a presently described composition, wherein the composition inhibits at least 50% of the demethylating activity of the demethylating enzyme as measured by levels of PP2A methyl esterification.

According to the present invention, the compositions can be used in methods of treating or preventing any disease, condition or disorder where defects in methylation metabolism appear to play a role as evidenced by an association of the disease, condition or disorder with plasma homocysteine levels that are elevated relative to normal plasma homocysteine levels. Such diseases, conditions or disorders include, but are not limited to, neurodegenerative diseases, disorders or conditions, such as Parkinson's disease, neuropsychiatric diseases, disorders or conditions, such as bipolar disorder, Alzheimer's disease, heart disease, arthritis, diabetes and certain cancers. The term "neurodegenerative" as used herein refers to a disease, condition or disorder marked by the loss or diminution of an original nerve cell function, and the term "neuropsychiatric" relates to organic and functional diseases, conditions or disorders of the nervous system.

According to yet another embodiment, the compositions can be used in methods of treating or preventing sleep disorders. Sleep disorders that can be treated using the compositions of the present invention include, but are not limited to, insomnia, narcolepsy, familial advanced sleep-phase syndrome (FASPS) and disruption to the circadian rhythm (e.g., jet lag).

The Clock (CLK) and Cycle (CYC) genes have been identified as positive regulators of cycle, whereas transcription factors Period (PER) and Timeless (TIM) negatively regulate cycle, and are repressors of CKL and CYC. PER and TIM are high at the beginning of night, and nuclear localization in the middle of the night inhibits CYC/CLK transcription factors, thus decreasing PER and TIM levels. In the morning hours, degradation of TIM and PER occurs, which promotes reactivation of PER and TIM expressions due to the release of the CYC/CLK/PER inhibitory complex. A new cycle starts through phosphorylation dependent degradation of PER. PER, TIM and CLK are phosphorylated in a circadian fashion by Doubletime (casein kinase 1ε) which targets for degradation and inhibits nuclear import and casein kinase II, which is important for nuclear localization. Phosphorylation controls nuclear localization and stability. PP1/PP2A, mainly PP2A, antagonizes PER degradation. PP2A is important for PER stability and nuclear translocation. PP1 regulates stability in a TIM dependent fashion.

PP2a dephosphorylates PER and TIM two main proteins in *drosophila* that control the circadian rhythm. Altering PP2A expression alters rhythms also affected by subunit expression (PER and TIM). See, Sathyanarayanan et al. 2004 Post-translational modification of *Drosophila* PERIOD protein by protein phosphatase 2A. Cell 116: 603. Human PERIOD2 (PER2) phosphorylated at Ser662 mutations at this site identified as familial advanced sleep phase syndrome (WASPS).

Mutated PP2A does not result in sleep rebound (longer REM sleep after sleep deprivation) which is instead associated with long term depression in the hippocampus (statement made in 26 J. B. Calais et al./Neurobiology of Learning and Memory 122 (2015) 19-27); Norman et al., 2000; Long-term depression in the hippocampus in vivo is associated with protein phosphatase-dependent alterations in extracellular signal-regulated kinase. Journal of Neurochemistry, 74(1), 192-198; Thiels et al., 2000 Protein phosphatase-mediated regulation of protein kinase C during long-term depression in the adult hippocampus in vivo. Journal of Neuroscience, 20(19), 7199-7207. Twins (homologue of B subunit) and Widerborst (homologue of B' subunit) are expressed in a circadian fashion; both which aid targeting of PER. PP2A dephosphorylates FREQUENCY in Neurospora. PP2A dephosphorylates and activates white collar complex (transcription factor of the circadian clock in Neurospora).

According to another embodiment of the present invention, the compositions can be used in methods of treating or preventing eye and vision disorders.

PP2A is implicated in visual transduction. PP2A translocation is light dependent; PP2A with B56e dephosphorylates and co-elutes with phosducin (a phototransduction protein in the retina) this is not observed with Balpha or B'(B56a). Brown, B. et. al. Light driven Translocation of the PP2A complex regulates Light/Dark Dephosphorylation of Phosducin and Rhodopsin. Biochemistry, 2002, 41(46); 13526-13538.

In the retina PP2A dephosphorylates CaBP4, which is a neuronal Ca(2+)-binding protein that is expressed in the retina and in the cochlea, and is essential for normal photoreceptor synaptic function. This action is light dependent. Haesseleer, F. et. Al. PP2A dephosphorylates CaBP4 and regulates CaBP4 function. Investi Ophthalmol Vis Sci. 2013, 54(2): 1214-1226. Mutations in CaBP4 are associated with congenital stationary night blindness type 2B.

PP2A is also implicated in retina cell survival. Retinal-derived 661W cells survival response through inhibition of PP2A and up regulation of Erk and Akt survival pathways. ROS production inhibits PP2A. Increased pTyr307 decreased methylation. This is also observed in retinal death in rd10 mice. Finnegan, S. et al. European Journal of Neuroscience. 2010; 32(3): 322-334.

PP2A is also implicated in eye development. B56e required for IGF/PI3K/Akt pathway, which is important for eye induction and also regulates Hedgehog important for eye field separation (*Xenopus*).

According to yet another embodiment, the compositions of the present invention can be used in methods of treating or preventing a mental disorder. For example, the presently disclosed compositions can be administered to subjects who exhibit abnormal one carbon metabolism (e.g., subjects who have disruptions in folate, methionine and choline pathways). The term "mental disorder" refers to diseases characterized as mood disorders, psychotic disorders, anxiety disorders, childhood disorders, eating disorders, personality disorders, adjustment disorder, autistic disorder, delirium, dementia, multi-infarct dementia and Tourette's disorder in the DSM-IV classification (Diagnosis and Statistical Manual of Mental Disorders, Fourth Edition, American Psychiatric Association, Washington D.C., 1994). In one particular embodiment, the compositions of the present invention are used to treat an autistic disorder.

According to yet another embodiment, the present compositions can be used in methods of treating a traumatic brain injury (TBI).

According to yet another embodiment, the present compositions can be used in methods of treating or preventing a cardiovascular disease or disorder. Cardiovascular diseases and disorders that can be treated using the compositions of the present invention include, but are not limited to, ischemic heart disease, non-ischemic heart disease, myocardial infarction, tachy-pacing induced non-ischemic heart disease, heart failure, atherosclerosis, ischemic stroke, problems with heart valves, and catecholaininergic-induced arrhythmia and symptoms thereof in a subject.

According to yet another embodiment, the present compositions can be used in methods of treating or preventing a metabolic disease or disorder. Metabolic diseases and disorders that can be treated using the compositions of the present invention include, but are not limited to, metabolic syndrome, insulin resistance, glucose intolerance, hyperglycemia, type I diabetes, type II diabetes, hyperlipidemia, hypertriglyceridemia, hypercholesterolemia, dyslipidemia, and polycystic ovary syndrome (PCOS), and symptoms thereof in a subject.

According to yet another embodiment of the present invention, a pharmaceutical preparation for promoting general health and well-being in a mammalian subject, including a human, is provided that includes a cognitive function-enhancing amount of an extract of the present invention and a pharmaceutically acceptable carrier.

In another embodiment, the subject exhibits, or is at risk for exhibiting, a skin disorder, medical condition or disease. In one embodiment, the subject desires to maintain healthy skin and prevent skin aging.

Another aspect of the present invention provides a method for inhibiting inflammation in a subject comprising administering to a subject an effective amount of a botanical extract.

In certain embodiments, the present invention provides methods of inhibiting inflammation, and uses of provided extracts and/or compositions in the treatment of inflammation. In certain embodiments, the present invention provides uses of provided extracts and/or compositions in the treatment of diseases that may benefit from edema inhibition, erythema inhibition and/or MPO inhibition, such as treating or lessening the severity of inflammatory diseases or disorders including, but not limited to, inflammation (acute or chronic asthma, autoimmune diseases, and chronic obstructive pulmonary disease (COPD) (e.g., emphysema, chronic bronchitis and small airways disease, etc.), inflammatory responses of the immune system, skin diseases (e.g., reducing acute skin irritation for patients suffering from rosacea, atopic dermatitis, seborrheic dermatitis, psoriasis), irritable bowel syndrome (e.g., Crohn's disease and ulcerative colitis, etc.), and central nervous system disorders (e.g., Parkinson's disease).

The present invention also relates to treating or lessening the severity of one or more diseases in which protein inhibitors that modulate the G-protein signaling cascade are known to play a role. Specifically, the present invention relates to a method of treating or lessening the severity of inflammatory diseases or disorders selected from inflammation (acute or chronic), inflammatory diseases or disorders (e.g., asthma, autoimmune diseases, and COPD including emphysema, chronic bronchitis and small airways disease, etc.), inflammatory responses of the immune system, skin diseases (e.g., reducing acute skin irritation for patients sufferine from rosacea, atopic dermatitis, seborrheic dermatitis, psoriasis), irritable bowel syndrome (e.g., Crohn's disease and ulcerative colitis, etc.), and Parkinson's disease, wherein the method comprises administering to a patient in need thereof a composition of the present invention.

In certain embodiments, the provided extracts of the present invention are capable of effectively inhibiting inflammatory responses that are mediated by G-proteins or GPCRs in neutrophils, macrophages and platelets. Thus, provided extracts are inhibitors of edema, erythema and myeloperoxidase and are therefore useful for treating one or more disorders associated with inflammatory diseases or disorders as described herein. In particular, the present invention encompasses the finding that certain extracts having superior in vivo activity than other extracts in the same class. Therefore, such extracts are administered to a subject suffering from or susceptible to one or more inflammatory diseases or disorders.

In certain embodiments, the treatment of inflammatory diseases or disorders is achieved using extracts without having the side effects of corticosteroids or NSAIDS.

In certain embodiments, such extracts are administered in vitro. In certain embodiments such extracts are administered in vivo.

Another aspect of the present invention is directed to methods of treating, preventing, or ameliorating inflammation by administering an effective amount of a provided extract.

In some embodiments, one or more inventive extracts, alone or together with one or more other pharmaceutically active agents, is used to whiten skin. In some such embodiments, the extract is applied topically.

In general, the actual quantity of provided extracts of the invention administered to a patient will vary depending on the severity and type of indication, the mode of administration, the particular extract used, the formulation used, and the response desired.

The dosage for treatment is administration, by any of the foregoing means or any other means known in the art, of an amount sufficient to bring about the desired therapeutic effect. Thus, an effective amount includes an amount of a provided extract (or mixture of provided extracts) or pharmaceutical composition of this invention that is sufficient to induce a desired effect, including specifically an anti-inflammation effect.

In general, the provided extracts of the present invention are highly active. For example, a provided extract can be administered at about 10 mg/kg to about 50 mg/kg body weight, depending on the specific provided extract selected, the desired therapeutic response, the route of administration, the formulation and other factors known to those of skill in the art.

In one embodiment, the botanical extract to be administered to subjects as described herein, is obtained from at least one fruit source selected from the group consisting of: juniper berry, schisandra, and strawberry. In another embodiment, the botanical extract is obtained from at least one seed source (e.g., avocado, black raspberry, blueberry, celery, cranberry, fennel, grape, guarana and red raspberry). In one particular embodiment, the seed source is selected from grape, guarana and red raspberry.

In another embodiment, the botanical extract is obtained from a least one root, bark or leaf source (e.g., maca root, goldenseal root, turmeric root, magnolia bark, pygeum bark, red raspberry leaf). In a still further embodiment, the root, bark or leaf source is turmeric root.

In another embodiment, the botanical extract is obtained from at least one natural source selected from the group consisting of: almond, cocoa powder, *Echinacea angustifolia*, prickly pear cactus and walnut. In one particular embodiment, the natural source is prickly pear cactus.

The compositions of the present invention may be in a form suitable for oral use, for example, as tablets, troches, lozenges, aqueous or oily suspensions, solutions, dispersible powders or granules, emulsions, hard or soft capsules, syrups or elixirs, pastes, gels or the like. Compositions intended for oral use may be prepared according to any known method, and such compositions may contain one or more agents selected from the group consisting of sweetening agents, flavoring agents, coloring agents, and preserving agents in order to provide pharmaceutically elegant and palatable compositions. Tablets may contain the active ingredient(s) in admixture with non-toxic pharmaceutically-acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch or alginic acid; binding agents, for example, starch, gelatin or acacia; and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They also may be coated for controlled delivery. For example, a "delayed release" dosage form releases a product or substance at a time other than promptly after administration. Examples of delayed-release systems include repeat-action tablets and capsules, and enteric-coated tablets where timed release is achieved by a barrier coating.

Compositions of the present invention also may be formulated for oral use as hard gelatin capsules, where the active ingredient(s) is(are) mixed with an inert solid diluent, for example, calcium carbonate, calcium phosphate or kaolin, or soft gelatin capsules wherein the active ingredient(s) is (are) mixed with water or an oil medium, for example, peanut oil, liquid paraffin, or olive oil.

The compositions of the present invention may be formulated as aqueous suspensions wherein the active ingredient(s) is (are) in admixture with excipients suitable for the manufacture of aqueous suspensions. Such excipients are suspending agents, for example, sodium carboxymethylcellulose, methylcellulose, hydroxy-propylmethylcellulose, sodium alginate, polyvinylpyrrolidone, gum tragacanth, and gum acacia; dispersing or wetting agents may be a naturally-occurring phosphatide such as lecithin, or condensation products of an alkylene oxide with fatty acids, for example, polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions also may contain one or more coloring agents, one or more flavoring agents, and one or more sweetening agents, such as sucrose or saccharin.

Compositions of the present invention may be formulated as oily suspensions by suspending the active ingredient in a vegetable oil, for example arachis oil, olive oil, sesame oil or coconut oil, or in a mineral oil, such as liquid paraffin. The oily suspensions may contain a thickening agent, for example, beeswax, hard paraffin or cetyl alcohol. Sweetening agents, such as those set forth above, and flavoring agents may be added to provide a palatable oral composition. These compositions may be preserved by the addition of an antioxidant such as ascorbic acid.

Compositions of the present invention may be formulated in the form of dispersible powders and granules suitable for composition of an aqueous suspension by the addition of water. The active ingredient in such powders and granules is provided in admixture with a dispersing or wetting agent, suspending agent, and one or more preservatives. Suitable dispersing or wetting agents and suspending agents are exemplified by those already mentioned above. Additional excipients, or example, sweetening, flavoring and coloring agents also may be present.

The compositions of the invention also may be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example, gum acacia or gum tragacanth, naturally-occurring phosphatides, for example soy bean, lecithin, and esters or partial esters derived from fatty acids and hexitol anhydrides, for example sorbitan monooleate, and condensation products of the partial esters with ethylene oxide, for example, polyoxyethylene sorbitan monooleate. The emulsions also may contain sweetening and flavoring agents.

The compositions of the invention also may be formulated as syrups and elixirs. Syrups and elixirs may be formulated with sweetening agents, for example, glycerol, propylene glycol, sorbitol or sucrose. Such formulations also may contain a demulcent, a preservative, and flavoring and coloring agents. Demulcents are protective agents employed primarily to alleviate irritation, particularly mucous membranes or abraded tissues. A number of chemical substances possess demulcent properties. These substances include the alginates, mucilages, gums, dextrins, starches, certain sugars, and polymeric polyhydric glycols. Others include acacia, agar, benzoin, carbomer, gelatin, glycerin, hydroxyethyl cellulose, hydroxypropyl cellulose, hydroxypropyl methylcellulose, propylene glycol, sodium alginate, tragacanth, hydrogels and the like.

Liquid based oral dosage forms, like their solid counterparts, can, in certain embodiments contain at least 0.1 mg of a provided extract. One skilled in the art will be able to properly formulate a liquid formulation containing an appropriate amount of a provided extract per fluidic ounce, depending on the additive or carrier selected.

Formulations suitable for buccal administration include tablets and lozenges comprising an extract in a flavored base, such as sucrose, acacia or tragacanth; and pastilles comprising the extract in an inert base, such as gelatin and glycerin or sucrose and acacia.

For topical administration formulations, any of a variety of creams, ointments, gels, cleansers, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a provided extract over a period of time. For example, gelatin, sodium carboxymethylcellulose and/or other cellulosic excipients may be included to provide time-release or slower-release formulations, especially for administration by subcutaneous and intramuscular injection. Other additives which may be used include vaseline, lanoline, polyethylene glycols, alcohols, transdermal enhancers, and combinations of two or more thereof.

In some embodiments, formulations suitable for topical application achieve transdermal delivery. Transdermal pharmaceutical devices include patches, occlusive dressings, occlusive formulations, hypodermic sprays, iontophoretic systems, gels and infusion pumps, all of which are well known in the art. A transdermal patch which includes a pharmaceutical may generally include a backing layer impermeable to the pharmaceutical, a reservoir to house the pharmaceutical, and an adhesive cover to be removed upon use of the patch and for adhesion to the skin of a patient.

Formulations suitable for transdermal administration may also be presented as medicated bandages or discrete patches adapted to remain in intimate contact with the epidermis of the recipient for a prolonged period of time. Representative examples of suitable transdermal patches include, for example, those developed by NeuroDerm Ltd (Israel) and/or that used to deliver estradiol, for example, those developed by Novogyne Pharmaceuticals. Formulations suitable for transdermal administration may also be delivered by iontophoresis (passage of a small electric current (~15 mA) to "inject" electrically charged ions into the skin) through the skin. For this, the dosage form typically takes the form of an optionally buffered aqueous solution of the active extract.

In practical use, a provided extract of the present invention can be combined as the active ingredient in an admixture with a pharmaceutical carrier according to conventional pharmaceutical compounding techniques. The carrier may take a wide variety of forms depending on the form of preparation desired for administration, for example, oral, parenteral (including intravenous), urethral, vaginal, nasal, dermal, transdermal, pulmonary, deep lung, inhalation, buccal, sublingual, or the like. In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets.

According to yet another embodiment of the present invention, a comestible for promoting general health and well-being in a mammalian subject, including a human, including one or more of the extracts described herein. According to another embodiment, the comestible is a beverage. According to another embodiment, the beverage is selected from the group consisting of a drink comprising water, a fruit drink, a coffee, a tea, an energy drink, a baby formula, an adult nutritional drink, a health drink, and a sports drink. According to another embodiment, the comestible is a food. According to another embodiment, the comestible is a cereal. According to another embodiment, the comestible is a chewing gum. According to another embodiment, the comestible is a candy.

EXAMPLES

Example 1—Preparation of Extracts

Various water-soluble oligosaccharides and starch in botanicals can reduce the specific activity of the extract, making the extract prone to bacterial contamination and growth; and change its appearance to sticky thick oil or to glassy caramel-looking substance. These properties make most of aqueous extracts difficult in manufacture (drying, emptying from reactor, drumming, etc.) and affect products shelf life and overall safety. Furthermore, removing various naturally occurring in a given botanic extract non-biologically active oils and lipids result in final extract to be a free flowing powder improving ease of manufacturing and blending into a product. Therefore, a process for manufacturing these extracts was designed to take these factors into account.

A raw botanical (10 g) was shaken with isopropyl alcohol (100 mL) in a flask at 65° C. for 16 hrs. The resulting isopropanolic extract was filtered and concentrated to dryness on a rotavap. The crude extract was heated with water (100ml) to remove caffeine and oligosaccharides, cooled to room temperature and collected by filtration. The solid was washed with hexane to remove oils and lipids to yield upon filtering and drying the final extract. The yields are listed in the Table 1.

TABLE 1

Extract's yields

| Fruit Extract | Yield (%) | Appearance |
|---|---|---|
| Almond | 4 | Off white |
| Avocado | 18 | Yellow semi-solid |
| Avocado Seed | 2 | Gold oil |
| Black Raspberry | 2 | Reddish gold |
| Blueberry | 1 | Pale yellow |
| Brazil Nut | 14 | Clear oil |
| Bromalin | <1 | Off white solid |
| Celery | 3 | Clear |
| Cocoa Butter | <1 | Clear/White oil |
| Cocoa Powder | <1 | Off white solid |
| Coconut | <1 | White solid |
| Coffee | 9 | Brown solid |
| Cranberry | 2 | Pale yellow |
| Echinacea Angustifolia | 11 | Clear |
| Fennel Seed | 2 | Pale gold oil |
| Goldenseal Root | 4 | Brownish yellow |
| Grape Seed | 8 | Reddish-brown solid |
| Grape Fruit (Oil) | <1 | Clear |
| Guarana Seed | 21 | Tan solid |
| Hazelnut | 4 | Clear oil |
| Juniper Berry | 7 | Yellow |
| Maca Root | 7 | Brown |
| Magnolia Bark | 11 | Carmel |
| Maqui Berry | 18 | Off-white |

TABLE 1-continued

Extract's yields

| Fruit Extract | Yield (%) | Appearance |
|---|---|---|
| Mulberry | 7 | Off-white |
| Pomegranate | <1 | Red sticky solid |
| Pygeum Bark | 11 | Off white |
| Prickly Pear Cactus | 14 | Dark green solid |
| Prickly Pear Fruit | 8 | Off white solid |
| Red Raspberry | 7 | Red solid |
| Red Raspberry Leaf | 3 | Tan |
| Schisandra | <1 | Tan |
| Strawberry | 2 | Pink |
| Walnut | 16 | Golden oil |

Example 2: Natural Extracts Effect on PP2A Methylation

Extracts, as shown in Tables 1-4 below, were created using isopropanol or toluene-based extraction methods at 65° C. as generally described in Example 1. These extracts were assayed for their ability to preserve the methylation status of PP2A AC dimer in the presence of protein phosphatase methylesterase-1 (PMF-1), using a radioactive filter binding assay. Methylated PP2A was made by incubating PP2A, protein phosphatase methyl transferase (PPMT) and [3H]-SAM for 1 hr. PME-1 was incubated with varying concentrations of botanical extracts prior to the addition of 50 nM of methylated PP2A. The reaction was allowed to continue for 30 minutes at room temperature. 10% TCA was added to stop the reaction and incubated for 1 hour. Remaining buffer was filtered and total counts remaining on the filter plate were measured using a scintillation counter. $IC_{50}$ values were generated from dose-response curves using a four-parameter logistic curve fit (SigmaPlot>.

The following results were obtained:

TABLE 1

Fruit extracts

| Fruit Extract | Estimated $IC_{50}$ (µg/mL) |
|---|---|
| Avocado | >25 |
| Blueberry | >50 |
| Bromalin | >50 |
| Cranberry | >30 |
| Coconut | >27 |
| Grape Fruit (Oil) | 25 |
| Juniper Berry | 5 |
| Maqui Berry | >10 |
| Mulberry | >10 |
| Pomegranate (Juice) | >27 |
| Prickly Pear Fruit | 15.6 |
| Schisandra | 6 |
| Strawberry | >5 |

TABLE 2

Seed extracts

| Seed Extract | Estimated $IC_{50}$ (µg/mL) |
|---|---|
| Avocado | 6 |
| Black Raspberry | 6 |
| Blueberry | 8 |
| Celery | 7 |
| Coffee | 5 |

TABLE 2-continued

Seed extracts

| Seed Extract | Estimated IC$_{50}$ (μg/mL) |
|---|---|
| Cranberry | 10 |
| Fennel | 1 |
| Grape | 0.4 |
| Guarana | 1.5 |
| Red Raspberry | 1 |

TABLE 3

Root, bark & leaf extracts

| Natural Extract | Estimated IC$_{50}$ (μg/mL) |
|---|---|
| Goldenseal Root | 4 |
| Maca Root | 3 |
| Magnolia Bark | 2 |
| Ppygum Bark | 3 |
| Red Raspberry Leaf | 2 |
| Tumeric Root | 2.9 |

TABLE 4

Other natural extracts

| Natural Extract | Estimated IC$_{50}$ (μg/mL) |
|---|---|
| Almond | >5 |
| Hazelnut | >10 |
| Cocoa Butter | 12.5 |
| Cocoa Powder | 6.25 |
| *Echinacea Angustifolia* | 4 |
| Prickly Pear Cactus | 52.5 |
| Walnut | 6 |

Only a subset of the botanical extracts tested demonstrated prevention of PP2A demethylation. Results indicate a distinction between extract categories, where the seed and root, bark and leaf categories consistently prevented PP2A demethylation with an IC$_{50}$ better than 5 μg/mL.

Example 3: Natural Extracts Effect on ROS Scavenging (Antioxidant)

Botanical extracts ability to prevent oxidation of ABTS by metmyoglobin was analyzed. The antioxidant capacity of select botanical extracts was evaluated in vitro using the ABTS (2, 2'-Azino-bis-[3-ehtylbenzthiazoline sulphonate]) antioxidant kit (Cayman Chemical Company; Ann Arbor, Mich.). Botanical extracts were incubated with both metmyoglobin and chomogen, ABTS. The reaction was initiated upon addition of hydrogen peroxide and the oxidation of the ABTS to ABTS was monitored via absorbance at 750 nm. EC$_{50}$ values were generated from dose-response curves using a four-parameter logistic curve fit (SigmaPlot), and are shown below in Table 5.

Example 4: Natural Extracts Effect on LPS-Induced Cytokine Release in PBMCs (Anti-Inflammatory)

Botanical extracts ability to inhibit the production of inflammatory cytokines TNF-α and IL-8 in PBMCs when challenged with lipopolysaccharides (LPS) through the administration of select botanical extracts was analyzed.

Normal human peripheral blood mononuclear cells (PBMCs) were obtained from a single donor, purchased from Zenbio (Research Triangle Park, N.C.). Cells plated at a seeding density of 0.33×10$^6$ cells/well. A two-hour pre-incubated period was performed with 150 μg/mL botanical extracts only fresh media in triplicates. Cells were then stimulated with 5 μg/mL LPS for 18 hours in the presence or absence of extract. After incubations, media supernatants were collected and analyzed by sandwich ELISA following the manufacturers protocols. Results are shown below in Table 5.

| Extract | Solvent | Inhibition of PP2A Demethylation IC$_{50}$ (μg/mL) | Prevention of ABTS Oxidation (Antioxidant) EC$_{50}$ (μg/mL) | +LPS TNF-a (pg/mL) 150 μg/mL Extract Average ± SEM | % Inhibition |
|---|---|---|---|---|---|
| Fennel Seed | Water | >25 | >500 | 78 ± 3.9 | 56.2 |
| | Isopropanol | 6 | >500 | 80.5 ± 9.2 | 62.5 |
| | Toluene | 1 | >500 | 68.9 ± 19 | 64.5 |
| Grape Seed | Water | 0.8 | 6.55 ± 0.8 | 147 ± 6.4 | 22.9 |
| | Isopropanol | 0.4 | 6.14 ± 2.6 | Cytotoxic | Cytotoxic |
| | Toluene | >12.5 | >500 | 118.2 ± 15 | 28.8 |
| Guarana Seed | Water | 8.7 | 23.2 | 58.5 ± 2.4 | 76.4 |
| | Isopropanol | 1.3 | 7.83 | 75 ± 2.8 | 69.5 |
| | Toluene | 1.1 | 67.7 | Cytotoxic | Cytotoxic |
| Prickly Pear Cactus | Isopropanol | 52.5 | 163 | 74.9 ± 4.3 | 59.1 |
| | Toluene | 4.5 | 174 | 143 ± 30.6 | -2.8 |
| Prickly Pear Fruit | Water | >50 | >500 | 53.3 ± 1.6 | 79.8 |
| | Isopropanol | 15.6 | >500 | 192 ± 36.9 | -9.5 |
| | Toluene | 6.2 | >500 | 97.9 ± 0.5 | 51 |
| Red Raspberry Seed | Water | >110 | 34.9 | 100 ± 5.3 | 45.6 |
| | Isopropanol | 1 | 8.01 ± 0.4 | 59.5 ± 2.1 | 84 |
| | Toluene | 1 | >500 | N.D. | N.D. |
| Turmeric Root | Water | >50 | >500 | 51.1 ± 0.75 | 80.7 |
| | Isopropanol | 2.9 | 11.4 | 36.8 ± 5.1 | 75 |
| | Toluene | 29 | 11.2 | 68.2 ± 6.5 | 65.1 |

All publications, patent and patent applications mentioned in this specification are incorporated herein by reference to the same extent as if each individual publication, patent or patent application was specifically and individually incorporated by reference.

While this invention has been particularly shown and described with references to preferred embodiments thereof, it will be understood by those skilled in the art that various changes in form and details can be made therein without departing from the scope of the invention encompassed by the appended numbered embodiments. Further, all embodiments included herein are given solely for the purpose of illustration and are not to be construed as limitations of the present invention, as many variations thereof are possible without departing from the spirit and scope of the invention.

The invention claimed is:

1. A method of preparing a botanical extract comprising:
    (a) contacting a raw botanical with a solvent having a dielectric constant ranging from about 2.3 to about 25 and allowing the mixture to reside for a sufficient time to obtain a crude extract;
    (b) filtering out remaining raw botanical and evaporating the solvent from the crude extract under reduced pressure to obtain a dried crude extract;
    (c) washing the dried crude extract from step (b) with a polar solvent having a dielectric constant of no less than 30, heating the resulting mixture, and allowing to cool to ambient;
    (d) collecting a filtrate from the cooled mixture from step (c); and
    (e) washing the collected filtrate from step (d) with a non-polar solvent having a dielectric constant of no more than 2.0; and
    (f) filtering and drying the mixture from step (e) to obtain the botanical extract.

2. The method of claim 1, wherein the solvent having a dielectric constant ranging from about 2.3 to about 25 is selected from isopropyl alcohol, toluene and ethyl acetate.

3. The method of claim 1, wherein the solvent having a dielectric constant ranging from about 2.3 to about 25 is evaporated from the crude extract by a rotary evaporator.

4. The method of claim 1, wherein the polar solvent having a dielectric constant of no less than 30 is water.

5. The method of claim 1, wherein the non-polar solvent having a dielectric constant of no more than 2.0 is selected from cyclohexane, hexane, heptane and isooctane.

* * * * *